(12) United States Patent
Iddan et al.

(10) Patent No.: US 7,643,865 B2
(45) Date of Patent: Jan. 5, 2010

(54) AUTONOMOUS IN-VIVO DEVICE

(75) Inventors: Gavriel J. Iddan, Haifa (IL); Zvika Gilad, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 344 days.

(21) Appl. No.: 11/025,604

(22) Filed: Dec. 30, 2004

(65) Prior Publication Data

US 2006/0004276 A1   Jan. 5, 2006

(51) Int. Cl.
*A61B 5/05* (2006.01)
(52) U.S. Cl. ............... 600/424; 600/302; 348/77
(58) Field of Classification Search ........ 600/407, 600/424, 153, 302, 172, 476, 547, 114, 350, 600/593, 582, 477, 109, 473, 160, 101; 348/81, 348/68, 76, 77, 301, 370; 128/899; 359/708; 385/12
See application file for complete search history.

(56) References Cited

U.S. PATENT DOCUMENTS

| | | | |
|---|---|---|---|
| 3,322,374 A | 5/1967 | King, Jr. | |
| 3,565,028 A * | 2/1971 | Hancks et. al. | 114/20.1 |
| 3,683,389 A | 8/1972 | Hollis | |
| 3,683,890 A | 8/1972 | Beal | |
| 3,971,362 A | 7/1976 | Pope et al. | |
| 4,027,510 A | 6/1977 | Hiltebrandt | |
| 4,177,800 A | 12/1979 | Enger | |
| 4,178,735 A | 12/1979 | Jackson | |
| 4,180,736 A | 12/1979 | Goodman | |
| 4,198,960 A | 4/1980 | Utsugi | |
| 4,239,040 A | 12/1980 | Hosoya et al. | |
| 4,262,632 A | 4/1981 | Hanton et al. | |
| 4,278,077 A | 7/1981 | Mizumoto | |
| 4,329,881 A | 5/1982 | Schloss | |
| 4,439,197 A | 3/1984 | Honda et al. | |
| 4,646,724 A | 3/1987 | Sato et al. | |
| 4,689,621 A | 8/1987 | Kleinberg | |
| 4,741,327 A | 5/1988 | Yabe | |
| 4,782,819 A | 11/1988 | Adair | |
| 4,803,992 A | 2/1989 | Lemelson | |
| 4,819,620 A | 4/1989 | Okutsu | |
| 4,844,076 A | 7/1989 | Lesho et al. | |
| 4,905,670 A | 3/1990 | Adair | |
| 4,936,823 A | 6/1990 | Colvin et al. | |

(Continued)

FOREIGN PATENT DOCUMENTS

DE   2928429   2/1980

(Continued)

OTHER PUBLICATIONS

U.S. Appl. No. 09/807,892, filed Jun. 6, 2001, Meron et al.

(Continued)

*Primary Examiner*—Brian Casler
*Assistant Examiner*—Nasir Shahrestani
(74) *Attorney, Agent, or Firm*—Pearl Cohen Zedek Latzer, LLP (57) ABSTRACT

The present invention may provide a system, method and device containing a motor. The motor may propel an in-vivo device by rotating a propeller situated for example outside of an outer shell of such device with an electromagnetic field generated by for example a plurality of electrical coils situated for example within such device.

20 Claims, 4 Drawing Sheets

U.S. PATENT DOCUMENTS

| | | |
|---|---|---|
| 4,940,997 A | 7/1990 | Hamlin et al. |
| 5,026,368 A | 6/1991 | Adair |
| 5,042,486 A | 8/1991 | Pfeiler et al. |
| 5,081,041 A | 1/1992 | Yafuso et al. |
| 5,109,870 A | 5/1992 | Silny et al. |
| 5,143,054 A | 9/1992 | Adair |
| 5,187,572 A | 2/1993 | Nakamura et al. |
| 5,195,702 A * | 3/1993 | Malvestuto, Jr. ............ 244/215 |
| 5,211,165 A | 5/1993 | Dumoulin et al. |
| 5,267,033 A | 11/1993 | Hoshino |
| 5,279,607 A | 1/1994 | Schentag et al. |
| 5,330,427 A | 7/1994 | Weissenburger |
| 5,368,015 A | 11/1994 | Wilk |
| 5,368,027 A | 11/1994 | Lubbers et al. |
| 5,395,366 A | 3/1995 | D'Andrea et al. |
| 5,398,670 A | 3/1995 | Ortiz et al. |
| 5,429,132 A | 7/1995 | Guy et al. |
| 5,435,761 A | 7/1995 | Shimamune et al. |
| 5,479,935 A | 1/1996 | Essen-Moller |
| 5,495,114 A | 2/1996 | Adair |
| 5,549,109 A | 8/1996 | Samson et al. |
| 5,558,640 A | 9/1996 | Pfeiler et al. |
| 5,604,531 A | 2/1997 | Iddan et al. |
| 5,607,435 A | 3/1997 | Sachdeva et al. |
| 5,643,175 A | 7/1997 | Adair |
| 5,662,587 A | 9/1997 | Grundfest et al. |
| 5,697,384 A | 12/1997 | Miyawaki et al. |
| 5,800,350 A | 9/1998 | Coppleson et al. |
| 5,819,736 A | 10/1998 | Avny et al. |
| 5,837,196 A | 11/1998 | Pinkel et al. |
| 5,913,820 A | 6/1999 | Bladen et al. |
| 5,929,901 A | 7/1999 | Adair et al. |
| 5,986,693 A | 11/1999 | Adair et al. |
| 5,993,378 A | 11/1999 | Lemelson |
| 6,043,839 A | 3/2000 | Adair et al. |
| 6,099,482 A | 8/2000 | Brune et al. |
| 6,135,729 A * | 10/2000 | Aber ........................ 417/420 |
| 6,149,581 A | 11/2000 | Klingenstein |
| 6,174,291 B1 | 1/2001 | McMahon |
| 6,228,048 B1 | 5/2001 | Robbins |
| 6,233,476 B1 | 5/2001 | Stormmer et al. |
| 6,240,312 B1 | 5/2001 | Alfano et al. |
| 6,285,897 B1 | 9/2001 | Kilcoyne et al. |
| 6,324,418 B1 | 11/2001 | Crowley et al. |
| 6,369,812 B1 | 4/2002 | Lyriboz et al. |
| 6,395,562 B1 | 5/2002 | Hammock et al. |
| 6,428,469 B1 | 8/2002 | Iddan et al. |
| 6,475,145 B1 | 11/2002 | Baylor |
| 6,488,694 B1 | 12/2002 | Lau et al. |
| 6,584,348 B2 | 6/2003 | Glukhovsky |
| 6,607,301 B1 | 8/2003 | Glukhovsky et al. |
| 6,632,171 B2 | 10/2003 | Iddan et al. |
| 6,632,175 B1 | 10/2003 | Marshall |
| 6,692,430 B2 | 2/2004 | Adler |
| 6,702,734 B2 | 3/2004 | Kim et al. |
| 6,709,387 B1 | 3/2004 | Glukhovsky et al. |
| 6,823,812 B2 * | 11/2004 | von Wolske ................ 114/286 |
| 6,939,290 B2 | 9/2005 | Iddan |
| 7,032,861 B2 * | 4/2006 | Sanders et al. ............ 244/23 A |
| 2001/0017649 A1 | 8/2001 | Yaron |
| 2001/0025135 A1 | 9/2001 | Naito et al. |
| 2001/0035902 A1 | 11/2001 | Iddan et al. |
| 2001/0051766 A1 | 12/2001 | Gazdzinski |
| 2002/0015952 A1 | 2/2002 | Anderson et al. |
| 2002/0103417 A1 | 8/2002 | Gazdzinski |
| 2002/0109774 A1 | 8/2002 | Meron et al. |
| 2002/0146368 A1 | 10/2002 | Meron et al. |
| 2002/0158976 A1 | 10/2002 | Vni et al. |
| 2002/0173718 A1 | 11/2002 | Frisch et al. |
| 2002/0177779 A1 | 11/2002 | Adler et al. |
| 2002/0198439 A1 | 12/2002 | Mizuno |
| 2003/0018280 A1 | 1/2003 | Lewkowicz et al. |
| 2003/0020810 A1 | 1/2003 | Takizawa et al. |
| 2003/0023150 A1 | 1/2003 | Yokoi et al. |
| 2003/0028078 A1 | 2/2003 | Glukhovsky |
| 2003/0040685 A1 | 2/2003 | Lewkowicz et al. |
| 2003/0043263 A1 | 3/2003 | Glukhovsky et al. |
| 2003/0045790 A1 | 3/2003 | Lewkowicz et al. |
| 2003/0069474 A1 | 4/2003 | Couvillon, Jr. |
| 2003/0077223 A1 | 4/2003 | Glukhovsky et al. |
| 2003/0092964 A1 | 5/2003 | Kim et al. |
| 2003/0114742 A1 | 6/2003 | Lewkowicz et al. |
| 2003/0117491 A1 | 6/2003 | Avni et al. |
| 2003/0120130 A1 | 6/2003 | Glukhovsky et al. |
| 2003/0151661 A1 | 8/2003 | Davidson et al. |
| 2003/0167000 A1 * | 9/2003 | Mullick et al. .............. 600/424 |
| 2003/0171648 A1 | 9/2003 | Yokoi et al. |
| 2003/0171649 A1 | 9/2003 | Yokoi et al. |
| 2003/0171652 A1 | 9/2003 | Yokoi et al. |
| 2003/0195400 A1 | 10/2003 | Glukhovsky |
| 2003/0195415 A1 | 10/2003 | Iddan |
| 2003/0208107 A1 | 11/2003 | Refael |
| 2003/0213495 A1 | 11/2003 | Fujita et al. |
| 2003/0214579 A1 * | 11/2003 | Iddan ......................... 348/81 |
| 2003/0214580 A1 | 11/2003 | Iddan |
| 2003/0216622 A1 | 11/2003 | Meron et al. |
| 2003/0229268 A1 | 12/2003 | Uchiyama et al. |
| 2004/0027459 A1 | 2/2004 | Segawa et al. |
| 2004/0027500 A1 | 2/2004 | Davidson et al. |
| 2004/0109488 A1 | 6/2004 | Glukhovsky et al. |
| 2004/0130640 A1 | 7/2004 | Fujimori et al. |
| 2004/0171914 A1 | 9/2004 | Avni |
| 2004/0258328 A1 | 12/2004 | Adler |
| 2005/0143623 A1 * | 6/2005 | Kojima ...................... 600/109 |

FOREIGN PATENT DOCUMENTS

| | | |
|---|---|---|
| DE | 34 40 177 | 6/1986 |
| FR | 2 688 997 | 10/1993 |
| IL | 126727 | 10/1998 |
| IL | 143258 | 5/2001 |
| IL | 143259 | 5/2001 |
| JP | 57-45833 | 3/1982 |
| JP | 3-289779 | 12/1991 |
| JP | 4109927 | 4/1992 |
| JP | 4144533 | 5/1992 |
| JP | 4-180736 | 6/1992 |
| JP | 5015515 | 1/1993 |
| JP | 6114037 | 4/1994 |
| JP | 6285044 | 10/1994 |
| JP | 7111985 | 5/1995 |
| JP | 7289504 | 11/1995 |
| JP | 2000342522 | 12/2000 |
| JP | 2001091860 | 4/2001 |
| JP | 2001095756 | 4/2001 |
| JP | 2001095765 | 4/2001 |
| JP | 2001104241 | 4/2001 |
| JP | 2001104242 | 4/2001 |
| JP | 2001104243 | 4/2001 |
| JP | 2001104244 | 4/2001 |
| JP | 2001104287 | 4/2001 |
| JP | 2001112709 | 4/2001 |
| JP | 2001112710 | 4/2001 |
| JP | 2001112740 | 4/2001 |
| JP | 2001137182 | 5/2001 |
| JP | 2001224551 | 8/2001 |
| JP | 2001224553 | 8/2001 |
| JP | 2001231744 | 8/2001 |
| JP | 2001245844 | 9/2001 |
| JP | 2002101990 | 1/2002 |
| JP | 2000342524 | 6/2002 |
| JP | 2000342525 | 6/2002 |
| JP | 2003260025 | 9/2003 |
| WO | WO 92-21307 | 12/1992 |

| | | |
|---|---|---|
| WO | WO 98-11816 | 3/1998 |
| WO | WO 98-29030 | 7/1998 |
| WO | WO 99-30610 | 6/1999 |
| WO | WO 99/32028 | 7/1999 |
| WO | WO 01-08548 | 2/2001 |
| WO | WO 01-10291 | 2/2001 |
| WO | WO 01/50941 | 7/2001 |
| WO | WO 01-65995 | 9/2001 |
| WO | WO 01/69212 | 9/2001 |
| WO | WO 01-87377 | 11/2001 |
| WO | WO 02/054932 | 7/2002 |
| WO | WO 02/055126 | 7/2002 |
| WO | WO 02/55984 | 7/2002 |
| WO | WO 02-67593 | 8/2002 |
| WO | WO 02-080763 | 10/2002 |
| WO | WO 02/094337 | 11/2002 |
| WO | WO 02-095351 | 11/2002 |
| WO | WO 02-102223 | 12/2002 |
| WO | WO 02/102224 | 12/2002 |
| WO | WO 03/003706 | 1/2003 |
| WO | WO 03/011103 | 2/2003 |
| WO | WO 03-021529 | 3/2003 |
| WO | WO 03/094723 | 11/2003 |
| WO | WO 2004-004540 | 1/2004 |
| WO | WO 2004/028336 | 4/2004 |
| WO | WO 2004/035106 | 4/2004 |
| WO | WO 2004-045395 | 6/2004 |
| WO | WO 2004-088448 | 10/2004 |

OTHER PUBLICATIONS

U.S. Appl. No. 10/200,548, filed Jul. 23, 2002, Glukhovsky et al.
U.S. Appl. No. 10/724,109, filed Dec. 1, 2003, Glukhovsky et al.
U.S. Appl. No. 10/166,025, filed Jun. 11, 2002, Lewkowicz et al.
U.S. Appl. No. 10/213,345, filed Aug. 7, 2002, Glukhovsky.
U.S. Appl. No. 60/297,761, filed Jun. 14, 2001, Lewkowicz et al.
U.S. Appl. No. 10/493,751, filed Apr. 27, 2004, Glukhovsky et al.
U.S. Appl. No. 60/299,178, filed Jun. 20, 2001, Glukhovasky et al.
U.S. Appl. No. 60/427,226, filed Nov. 19, 2002, Palti.
U.S. Appl. No. 60/354,926, filed Feb. 11, 2002, Iddan.
U.S. Appl. No. 60/376,006, filed Apr. 25, 2002, Lewkowicz et al.
U.S. Appl. No. 60/310,232, filed Aug. 7, 2001, Glukhovsky.
The Haidelburg pH Capsule System Telemetric Fasting Gastric Analysis, Heidelburg international incorporated.
Heidelberger Kapsel—ein Kleinstesender fur die pH-Messung im Magen Lange, et al, Telefunken-Zeitung, Jg 36 (1963) Heft 5, pp. 265-270.
New smart plastic has good memory—Turke, European Medical Device Manufacturer, devicelink.com.
Robots for the future—Shin-Ichl. et al. http://jin jcic or jp/nipponala13/sp05 html. printed Nov. 29, 2001.
The Radio Pill, Rowlands, et al, British Communications and Electronics, Aug. 1960, pp. 598-601.
Video Camera to "Take"—RF System Lab, Dec. 25, 2001.
Wellesley company sends body montiors into space—Crum, Boston Business Journal 1998.
www rfnorida com—NORIKA3, printed on Jan. 1, 2002.
Wireless transmission of a color television moving image from the stomach usning a miniature CCD camera, light source and microwave transmitter Swain CP. Gong F, Mills TN Gastrointest Endosc 1997;45:AB40, vol. 45, No. 4, 1997.
In Pursuit of the Ultimate Lamp, Craford et al, Scientific American Feb. 2001.
Manual of Photogrammetry, Thompson (Ed.), Third Edition, vol. Two Copyright 1944, 1952, 1966 by the American society of Photogrammetry.
www.jason.net/tinycam.htm, © 2001, printed Dec. 19, 2001.
www middleeasthealthmag com/article2.htm—Review proves the value of computers, © 2001 printed Nov. 29, 2001.
www pedinc com Personal electronic devices © 1997.
BBC News Online—Pill camera to 'broadcast from the gut', Feb. 21, 2000, www news.bbc.co uk printed Oct. 22, 2002.
International Search Report for PCT/IL99/0554 dated Apr. 4, 2000.
Supplementary partial European Search Report, Mar. 19, 2004.
International Search Report of PCT/IL02/00391, dated May 19, 2003.
Katgraber F, Glenewinkel F, Flachler S, Int J. Legal Med 1998; 111(3) 154-8.
Wang et al., "Integrated Micro-Instrumentation for Dynamic Monitoring of the Gastro-Intestinal Tract", Presented at IEEE Instrumentation and Measurment Technology Conference, May 2002, Anchorage Ak, USA, www see ed ac uk/Nsa publications.html.
Evaulation of the heidelberg pH capsule: Method of Tubeless Gastric Analysis, Yarbrough, III et al., The American Journal Of Surgery, vol. 117, Feb. 1969, pp. 185-192.
Bio-Medical Telemetry: Sensing and Transmitting Biological Information from Animals and Man, R. Stuart Mackay, John Wiley and Sons, New York 1970, pp. 244-245.
Rowell, Nancy D . Endoscopes Go Wireless, Biophotonics in Action, Photonics Spectra, pp. 60-62, Mar. 200.
Transit times for the Capsule Endoscope, Gastrointestinal Endoscopy, Apr. 2001: vol. 53:AB122.
www.rfsystemlab com—Listing on the N.Y stock exchange 2001.
PCT Search Report International Application No. PCT/IL02/00386 International Filing Date: May 19, 2002.
PCT International Search Report in International Application No. PCT/IL03/00339 Mailing date: Oct. 6, 2003.
U.S. Appl. No. 10/879,054, filed May 30, 2004, Gilad, et al.
U.S. Appl. No. 10/166,025, filed Jun. 11, 2002, Lewkowicz.

* cited by examiner

AUTONOMOUS IN-VIVO DEVICE

FIELD OF THE INVENTION

The present invention relates to a motor, to methods of production thereof, and to uses thereof. Typically the invention relates to a brushless motor that may be used in-vivo, possibly in miniature devices.

BACKGROUND OF THE INVENTION

In-vivo sensing devices, such as for example autonomous in-vivo capsules may be moved through a body lumen by periodic forces such as for example peristalsis in the gastrointestinal tract. In certain areas of a body lumen, such as for example a small intestine, such forces may be sufficient to move a device through the lumen. In other areas however, such as for example a large intestine, such forces may be less frequent and may leave a device in a single position for long periods of time. Sensing the entire lumen of, for example, the large intestine may be, for example, erratic as well as time consuming. The area of the lumen about which data may be collected may also be limited to the point around which the device came to rest.

SUMMARY OF THE INVENTION

According to embodiments of the present invention, an autonomous in-vivo device may include a rotor, a plurality of electric coils to generate an electromagnetic field from inside the in-vivo device around the rotor, and a switch to direct current to one or more coils at a time. In some embodiments of the present invention the rotor may be a propeller to propel the in-vivo device through a body lumen.

According to embodiments of the present invention a method of propelling an in-vivo device may be provided. For example, an electromagnetic field from within the device set around the propeller may be generated. The electromagnetic field may serve to rotate the propeller. In one embodiment of the present invention, fluids within the body lumen may be directed to the propeller through channels incorporated within the in-vivo device.

In other embodiments of the present invention a system for controlling a rotor within an in-vivo device may be provided. According to one embodiment of the present invention the system may include an in-vivo sensing device with a rotor and a transmitter, an external transceiver and/or receiver.

BRIEF DESCRIPTION OF THE DRAWINGS

The present invention will be understood and appreciated more fully from the following detailed description taken in conjunction with the drawings in which.

It will be appreciated that for simplicity and clarity of illustration, elements shown in the figures have not necessarily been drawn accurately or to scale. For example, the dimensions of some of the elements may be exaggerated relative to other elements for clarity, or several physical components may be included in one functional block or element. Further, where considered appropriate, reference numerals may be repeated among the figures to indicate corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well-known features may be omitted or simplified in order not to obscure the present invention.

Figure 1:
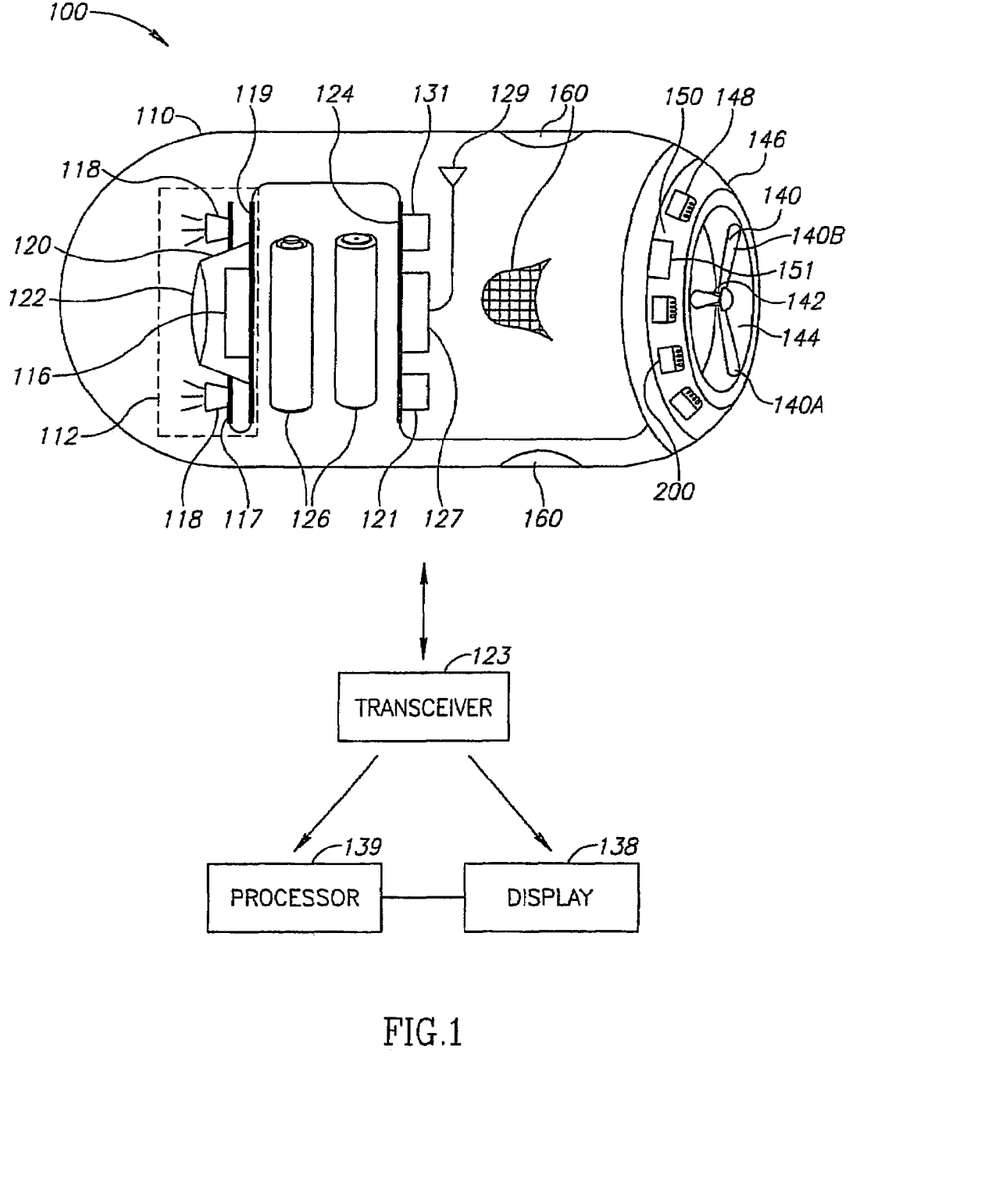
FIG. 1 is a schematic diagram of an in-vivo device with a propeller driven by an electric motor in accordance with an embodiment of the invention.

Reference is made to FIG. 1, a schematic diagram of an in-vivo device with an in-vivo, typically electric motor in accordance with an embodiment of the invention. In some embodiments of the present invention, a propeller device may be driven by the in-vivo motor. In other embodiments of the present invention, one or more other components of a device may be driven by the in-vivo motor, for example, a sampling probe, a door for a chamber, or other in-vivo component. Device 100 may include a sensing device such as for example an imaging device 112 within an outer shell or housing 110 constructed and operative in accordance with an embodiment of the invention. Housing 110 may be, for example, spherical, ovoid, capsule shaped or any other suitable shape and may be partially deformable. Imaging device 112 may typically include at least one sensor such as for example imaging sensor 116, which may be or include for example a charge coupled device (CCD) or a complementary metal oxide semiconductor (CMOS) image sensor. Image sensor 116 may be supported for example, on circuit board 119. In FIG. 1 the imaging device 112 may include, for example a lens 122 and a lens holder 120. One or more (e.g., a pair or a ring) illumination sources 118, such as light emitting diodes (LEDs), may illuminate areas to be imaged by the imaging sensor 116. Illumination sources 118 may be supported on circuit board 117. Other suitable positions for imaging sensor 116 and illumination sources 118 may be used and other suitable circuit boards and shapes of a housing 110 may be used. Device 100 may include a circuit board 124 or other suitable substrate that may contain one or more components and/or circuitry, e.g. switches and/or a controller that may have a capacity to control or regulate one or more components in device 100, and one or more power sources such as for example batteries 126. In some embodiments device 100 may include a transmitter 127, such as for example a wireless transmitter and an antenna 129. Device 100 may include a receiver 121 that may receive signals from, for example, an external source, such as control signals transmitted from, for example, an operator and a controller 131 that may control responses of device 100 to such signals. In some embodiments of the present invention, transmitter 127, receiver 121 and controller 131 may be integrated into a single component, for example, a transceiver or other component. In other embodiments, more or less components may be integrated into a single component. Device 100 may transmit signals and/or data to, for example, an external transceiver 123 where such signals, sensory data or images may be stored or further processed for analysis, for example, by processor 19 and/or viewed on an external display 138, such as for example a monitor. In some embodiments transceiver 123 may include only receiving capabilities. In some embodiments, transmitter 127 for example may transmit image signals to the external receiving unit so that images may be viewed for example on-line and in real time as the device 100 may pass through a body lumen. Other suitable viewing methods may be used. In some embodiments, an operator such as for example a viewer of an image on display 138 may control one or more of the functions of device 100 by for example transmitting signals and/or input commands to, for example, receiver 121. A wire 152, or other lead, or other electrical connection may connect board 124 with other components of device 100 such as for example board 150.

In some embodiments of the present invention, device 100 may include a screw, propeller, fan, or rotor 140 that may be attached, for example fixed or rotatably attached, to a shaft 142. In other embodiments other suitable components, besides a propeller may be engaged to shaft 142 for functions other than and/or including propulsion. Rotor 140 may be situated inside for example a crater-shaped hub 144 that may form for example the center of a doughnut-shaped ring 146 that may surround the hub 144. Dimensions of hub 144 may be such that rotor 140 may rotate freely within ring 146. In some embodiments, hub 144 and ring 146 may be shaped similar to the dimple or punt at the bottom of a wine bottle. Shaft 142 may be rotatably fixed to the base of ring 146 so that it may rotate freely. The base of ring 146 may in some embodiments be approximately 9 to 13 mm in diameter and be recessed approximately 5 to 10 mm from the outermost portion of ring 146. Other shapes and configurations may be used. In some embodiments, rotor 140, e.g. propeller may be or include one or more permanent magnets having a north and south end. Sealed or enclosed within ring 146 may be one or more electrical coils 148. Coils 148 may in some embodiments be held by and connected to a circuit board 150, or other substrate or other holder and or support that may provide electrical connections to coils 148. Circuit board 150 may include or be connected to circuitry, e.g the controller 131 and/or a switch 151, such as for example a reed switch that may control or regulate the flow of current among coils 148. Support or circuit board 150 may be in electrical communication with for example circuit board 124 and/or batteries 126. One or more intake ducts 160 in for example along the housing may channel liquids from an area around device 100 into hub 144.

In operation, rotor 140, ring 146 and coils 148 may be configured as components of for example an electric motor, such as for example a brushless electric motor, such that rotor 140 may serve as the rotor of such motor, ring 146 may serve as the stator of such motor, and coils 148 may carry current, for example, providing a magnetic force that may influence the orientation of propeller or shaft 42 and cause it to rotate. For example, an AC current passing through each of coils 48 with a phase lag may cause an alternating magnetic force that may, for example, rotate magnetic blades 140A and 140B. In other embodiments a DC current supplied to each of the coils in a sequence may provide an alternating magnetic force that may rotate the magnetic blades 140A and 140B. Other suitable methods may be used to drive rotor 140 and/or shaft 142. Liquid may flow or be drawn from an in-vivo environment into ducts 160, and may be and channeled through to hub 144 where such liquid may be forced out by rotor 140, thereby providing thrust to device 100. In some embodiments the speed of rotor 140 may be controlled by for example a timer with a switch or a controller on for example board 124, or by for example an operator or external controller, e.g. included in an external transceiver 123 or processor 139 that may transmitting signals to device 100. In other embodiments, one blade, for example, blade 140A may be made to be heavier than another blade 140B. Such lack of balance in the weights of the blades 140A and 140B may initiate, for example, a secondary circular swaying motion of device 100 as it may advance forward or backwards during propulsion. In some embodiments of the present invention, it may be desirable to initiate a swaying motion of the device so as to increase the field of view of for example the imager 116 or other sensing device during propulsion through a body lumen.

Device 100 may include components and operate similarly to the imaging systems described in U.S. Pat. No. 5,604,531 to Iddan, et al., WO 01/65995 and/or WO 02/054932, each assigned to the common assignee of the present application and each hereby incorporated by reference. Furthermore, a reception, processing and review system may be used, such as in accordance with embodiments of U.S. Pat. No. 5,604,531 to Iddan, et al., WO 01/65995 and/or WO 02/054932, although other suitable reception, processing and review systems may be used.

Rotor 140 may be constructed of or coated with for example stainless steel or other metallic alloy that may be magnetized or otherwise made reactive to magnetic force. Other suitable materials may be used. Rotor 140 may be of fixed pitch or variable pitch, and may have more than two blades. Rotor 140 may be magnetized using known methods such that one end 140A is positive and another end 140B is negative. Propellers with a larger number of blades may also be possible. For example, for a capsule with dimensions of 20 to 35 mm in length, 11 to 14 mm diameter, and weighing approximately 2.5-3.5 grams, a propeller of 4 to 8 mm rotating at, for example, 40 to over 1000 revolutions per minute may be sufficient to propel a capsule at a rate of 0.5 to 10 cm/s through a standing liquid. Other speeds, sizes and constructions of rotor 140 are possible.

Rotor 140 may be fixed to and extend from shaft 142. In some embodiments, rotor 140 may be rotatably fixed to the housing at the base of hub 144. In some embodiments, rotor 140 may be constructed of non-metallic substances.

Ring 146 may be or be constructed from a hollowed portion of housing 110. Outer shell of ring 146 may be constructed of, resin or other suitable material, through which an electromagnetic force may pass. In some embodiments, ring 146 may be shaped as a laterally bisected and hollowed torus (shaped as a sliced bagel that has been emptied of all but its outer crust). Ring 146 may take other shapes such as for example a square, rectangle, etc.

Figure 2A:
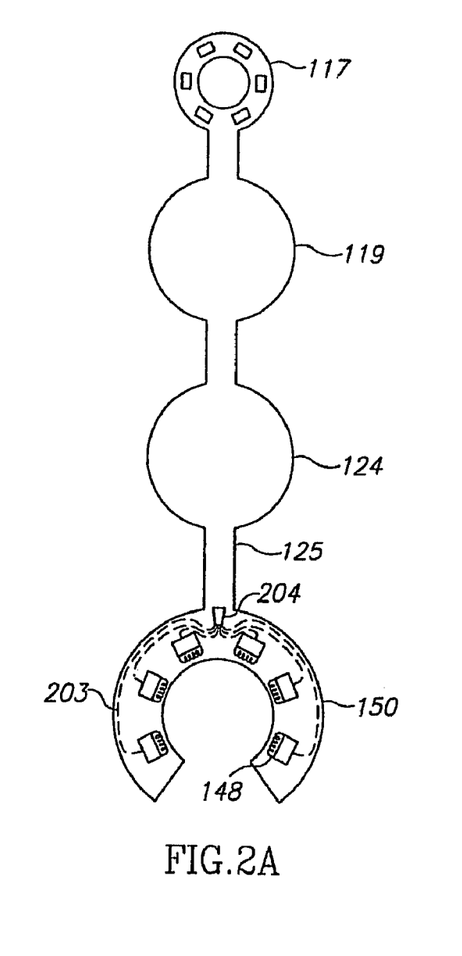
FIG. 2A is a schematic diagram of a circuit board with electrical coils in accordance with an embodiment of the invention.

Reference is made to FIG. 2A, a schematic diagram of a circuit board with rigid and flexible sections having one section with electrical coils in accordance with an embodiment of the invention. Rigid circuit boards sections 117, 119, and 124 and flexible circuit boards 125 and 150 may be configured as is described in embodiments of the invention described in publication WO 02/102224 entitled "In-vivo Device with a Circuit Board having Rigid Sections and Flexible Sections", and in U.S. patent application Ser. No. 10/879,054 filed on Jun. 30, 2004 and entitled "In-vivo Device having Flexible Circuit Board and Method of Manufacturing Thereof", each assigned to the common assignee of this application and each incorporated in their entirety by reference herein. In one embodiment of the present invention, circuit board 117 may support one or more illumination sources 118. Circuit board 119 may support, for example imager 116, and circuit board 124 may support, for example, one or more components such as transmitter 127. Other suitable components may be supported by one or more circuit board section and other suitable number of circuit boards sections may be used. In some embodiments rigid sections may be alternatively flexible sections. In some embodiments, one or more coils 148 may be attached to and protrude from board 150 and board 150 may be connected by a flexible circuit board and/or connection 125 to circuit board 124. A controller 204 embedded to board 150 may be used (e.g. in addition to or instead of controller 131) to control current through coils 148. Coil current drive lines 202 may connect coils 148 to a controller 204 via a switch. In other embodiments a switch may be integral to controller 204 or may not be needed. Sensors 200, as may be suitable for brushless electric motors may be situated on board 150 at various points between or among coils 148 and may be connected to controller 204 through, for examples, lines 203. In some embodiments, board 150 may be shaped as a flattened ring that may be fitted over the hollowed area of ring 146. In some embodiments, board 150 may be ring shaped or coned shape so that coils 148 that may protrude upwards from board 150, may face inwards towards hub 144. Angling of board 150 may direct a greater portion of the electromagnetic field created by coils 148 towards rotor 140. In some embodiments, coils 148 may be held in housing 110 without a board 150, and may be in electrical communication with a controller 131 and a power source 126.

Board 150 may be preferably completely enclosed within housing 110 so that no part of board 150 and coils 148 may come in contact with the liquids or other matter in an in-vivo environment.

In some embodiments, controller 204 may be built into board 150 or attached for example perpendicular to the bottom of board 150. Controller 204 may include a reed switch or other suitable components for switching on/off the current to one or more of coils 148 so as to for example, regulate and alternate the current in a brushless electric motor. Controller 204 may alternate the flow of current through coils 148 so that rotor 140 may rotate smoothly within hub 144. In some embodiments the rotation of rotor 140 may be reversed by changing the order of the alternation of current in coils 148. The rotation of rotor 140 may be, for example, controlled to be clockwise or counter-clockwise to either advance device 100 forwards or backwards. In some embodiments rotor 140 may be sequentially rotated forward and backwards to for example jiggle device 100 out of a stuck position.

In some embodiments a current of, for example, 5 to 15 mAmp passing through coils 148 may be sufficient to drive rotor 140 through a body lumen at a rate of approximately 40 to over 1000 revolutions per minute. Other suitable speeds may be used and other suitable currents may be used.

Coils 148 may take shapes other than coils and may be constructed from any suitable conductive material through which an AC or DC current may be passed in order to create an electromagnetic field and/or electromagnetic force.

One or more ducts 160 may be configured into the shell of housing 110. Ducts 160 may open along the outside of housing 100 anterior to the end of the device 100. Ducts 160 may channel liquid or other matter in an inward and posterior direction toward one or more openings in the ring 146 or elsewhere on outer shell of housing 110 that may be for example anterior to rotor 140. The channel of duct 160 may be beveled from the sides of housing 110 to the opening below ring 146. In some embodiments the outer opening of duct 160 along the side of device 100 may be covered by a screen to avoid solid matter from clogging duct 160 or rotor 140.

Figure 2B:
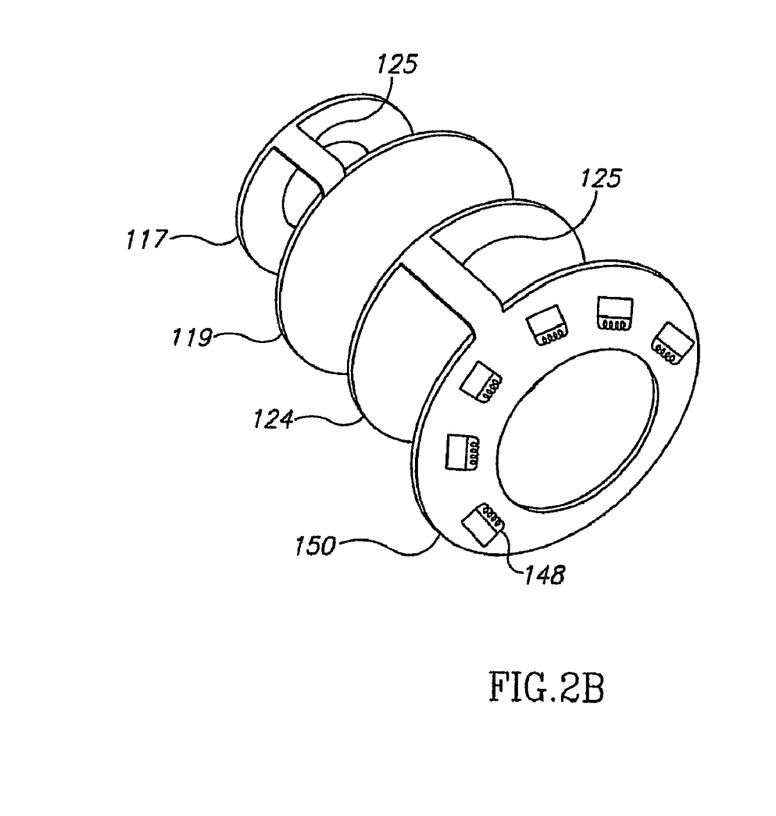
FIG. 2B is schematic diagram of a folded circuit board with rigid and flexible sections having one section with electrical coils in accordance with an embodiment of the invention.

Reference is now made to FIG. 2B showing a schematic diagram of a folded circuit board with rigid and flexible sections having one section with electrical coils in accordance with an embodiment of the invention. Flexible section 150 may support one or more coils 148. Between rigid section 119 and 124 one or more batteries 126 may be positioned and contacts provided in section 119 and 124 may provide electrical contact between power source 126 and other components. Rigid section 117 may support one or more illumination devices. Flexible sections 125 may provide electrical communication between the various circuit board sections and the power source 126.

Figure 3:
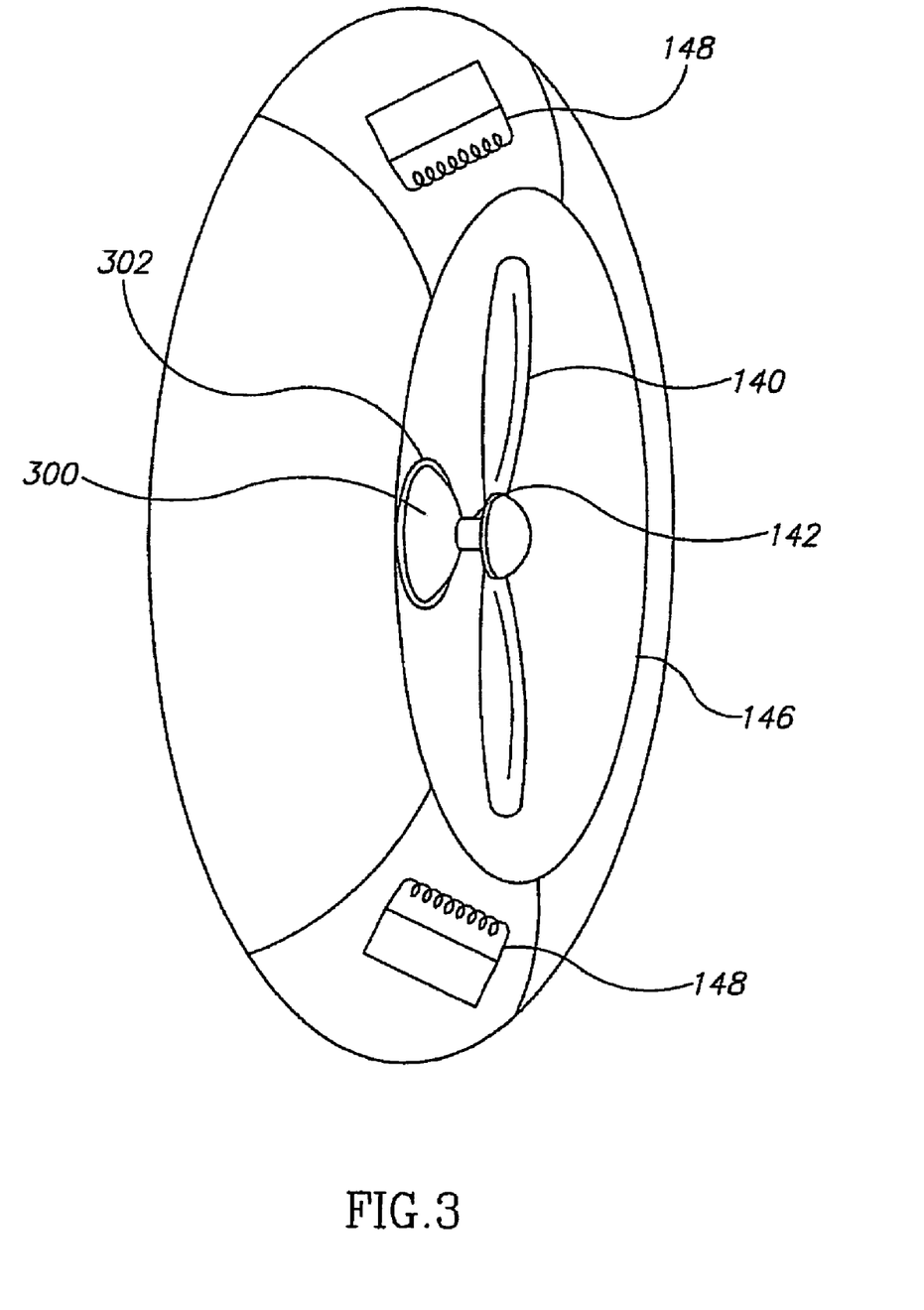
FIG. 3 is a schematic diagram of a propeller shaft with a ball and socket in accordance with an embodiment of the invention.

Reference is made to FIG. 3, a schematic diagram of a propeller shaft with a mechanical joint, for example a ball 300 and socket 302 joint in accordance with an embodiment of the invention. In some embodiments, shaft 142 may be attached to, or may include for example a ball 300 and socket 302 joint that may permit shaft 142 to pivot such that there may be a change in the angle of orientation of rotor 140 relative to the end of device 100. In some embodiments a ball 300 and socket 302 may join rotor 140 to shaft 142 so that the angle of rotor 140 may be changed without changing the angle of shaft 142. In some embodiments, the relative strength of the current, whether negative or positive, passed through the coils 148 on a particular side of ring 146 may be increased compared to the strength of current passed through coils 148 on another side of ring 146. Such changes in the relative strength of current may cause rotor 140 to tilt towards one direction, for example, the direction toward the side with greater current flowing through a coil 148. Such a tilt may in some embodiments modify a direction of the thrust produced by rotor 140, and hence the vector of device 100. In some embodiments, an external operator may control such changes in current to control the tilt of such rotor 140 and the direction of thrust generated by rotor 140. Other methods of tilting or reorienting the direction of thrust from rotor 140 may be possible.

Figure 4:
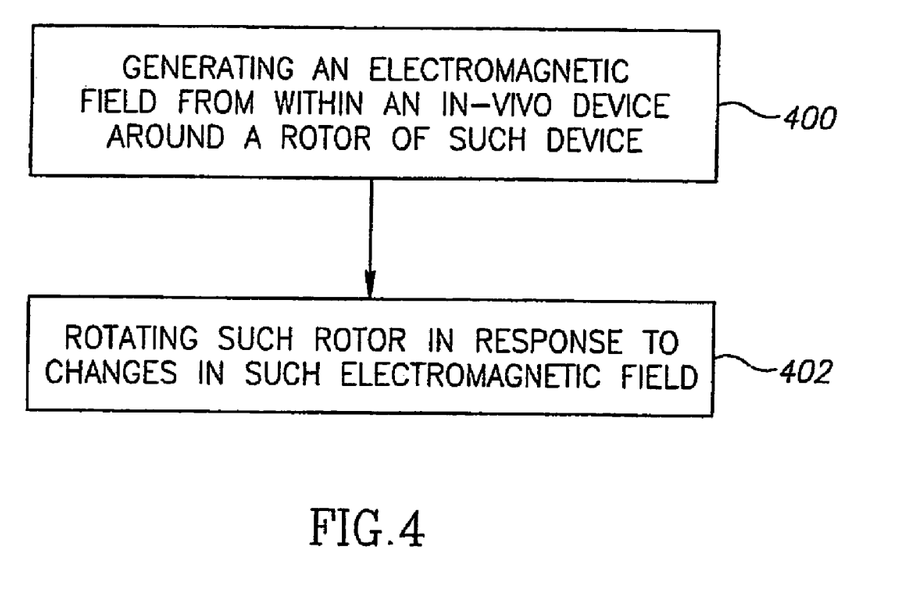
FIG. 4 is a flow chart of a method in accordance with an embodiment of the invention.

Reference is made to FIG. 4, describing a flow chart of a method in accordance with an embodiment of the invention. In block 400, an electromagnetic field and/or force may be generated from within an in-vivo device around a shaft, fan, screw or propeller attached to such device. In some embodiments, the electromagnetic field may be generated by one or more electrical coils 148 that may be positioned inside a housing 110 of the in-vivo device 100, for example, around a hub 144 of such device 100. In some embodiments such coils 148 may be attached to one or more circuit boards 150 that may be folded or looped into the shape of a ring. In some embodiments such circuit board 150 may be a flexible circuit board. In some embodiments the circuit board may be angled so that the electrical coils face or partially face inwards towards the hub at the center of the circuit board outside of the device.

In block 402 a rotor (e.g., a propeller) may rotate within such electromagnetic field in response to changes in the field. In some embodiments AC and/or DC current may directed to one or more electrical coils at a time so as to provide an alternating electromagnetic field and/or force. The propeller may include a permanent magnet with a north and south side. The alternating current in the coils may cause the propeller to rotate similar to the rotation of a rotor in a brushless motor. In some embodiments the propeller may be attached to a shaft 142 that the shaft may be rotatably secured for example to the posterior of the device. In some embodiments the rotor 140 may be attached to for example a ball 300 and socket joint 302 that may permit the rotor 140 to tilt for example towards an electric coil 148 that may carry a relatively greater current than do others of the electrical coils 148 surrounding the propeller. Other suitable methods of altering the direction of, for example, rotor 140 may be used. Other steps or series of steps may be used. In other embodiments of the present invention, shaft 142 may be used to drive other components of in-vivo device 100.

While the present invention has been described with reference to one or more specific embodiments, the description is intended to be illustrative as a whole and is not to be construed as limiting the invention to the embodiments shown. It is appreciated that various modifications may occur to those skilled in the art that, while not specifically shown herein, are nevertheless within the true spirit and scope of the invention.

We claim:

1. An autonomous in-vivo device, comprising:
   a capsule;
   said capsule comprising a rotor, being a propeller, rotatably connected to a shaft;
   a plurality of electric coils positioned around said rotor;
   a controller to control current flow through said electric coils causing the rotor to rotate and causing the rotor to tilt towards at least one of said electric coils thereby providing direction and a forward or backward thrust of said device.

2. The device as in claim 1, comprising a duct to channel liquid to said rotor.

3. The device as in claim 1, wherein said rotor includes at least one permanent magnet.

4. The device as in claim 1, wherein said plurality of electric coils are enclosed within an outer shell of said device.

5. The device as in claim 4, wherein said outer shell has a tows shaped end.

6. The device as in claim 1, wherein said plurality of electric coils are mounted on a flexible circuit board.

7. The device as in claim 1, wherein the rotor shaft is attached to a ball and socket joint.

8. A method of propelling an in-vivo device, comprising:
   providing an autonomous in-vivo capsule imaging device within a gastro-intestinal tract of a subject;
   generating an electromagnetic field from a plurality of electric coils positioned within said device around a propeller of said device;
   rotating said propeller in response to changes in said field to provide forward thrust or backward thrust for said device; and
   tilting said propeller towards at least one of said electric coils in response to changes in said field to provide a direction of said forward or backward thrust.

9. The method as in claim 8, comprising channeling fluids in an in-vivo area to said propeller.

10. The method as in claim 8, wherein said tilting comprises changing strength of current flow through a first coil relative to strength of current flow through a second coil where the first coil is positioned on a first side of said propeller and the second coil is positioned on a second side of said propeller.

11. The method as in claims 10, comprising transmitting a signal from an external operator to said in-vivo device to change said strength of said current in said first coil.

12. The method as in claim 8, comprising changing a direction of a thrust from said propeller.

13. A system comprising:
   an in-vivo capsule imaging device comprising:
      a sensor for generating data;
      a rotor, being a propeller, providing forward thrust or backward thrust when caused to rotate;
      a plurality of electric coils positioned around said rotor;
      a controller to control current flow through said plurality of electric coils causing the rotor to rotate and tilt towards at least one of said plurality of electric coils where said tilting provides a direction for a forward or backward thrust;
      a transceiver for receiving data from the sensor and transmitting said data; and
      an external transceiver for receiving data from the device and transmitting signals to the device.

14. The system as in claim 13, wherein said in-vivo device comprises a duct to channel a liquid to said rotor.

15. The system as in claim 13, wherein said rotor is connected to said device with a ball and socket joint.

16. The system as in claim 13, comprising a flexible circuit board upon which said electrical coils are arranged.

17. The system as in claim 13, comprising a housing in which said electrical coils are completely enclosed.

18. The device of claim 1, wherein the controller changes strength of current on a first of said electric coils with respect to current on a second of said electric coils, and to thereby tilt rotor relative to said electric coils to control the direction of thrust.

19. The method of claim 8, wherein tilting said propeller comprises changing strength of said field at certain portions around said tiltable propeller relative to other portions around said tiltable propeller.

20. The system of claim 13, wherein said in vivo device further comprises:
   a controller coupled to said electric coils via at least one switch to change strength of current in coils on a first side of the rotor with respect to current in coils on a second side of the rotor to thereby tilt said rotor relative to said device; and
   wherein said plurality of electric coils is used to generate an electromagnetic field from inside said device around said rotor.

* * * * *